United States Patent [19]

Bloore

[11] Patent Number: 5,580,243
[45] Date of Patent: Dec. 3, 1996

[54] REMOVABLE ORTHODONTIC ALIGNER WITH EYELET ARM SPRINGS

[76] Inventor: John A. Bloore, 808 Franklin St., Santa Monica, Calif. 90403

[21] Appl. No.: 456,531

[22] Filed: Jun. 1, 1995

[51] Int. Cl.⁶ ..................................................... A61C 3/00
[52] U.S. Cl. .................. 433/6; 433/7; 433/17; 433/18; 433/21
[58] Field of Search .......................................... 433/6, 18

[56] References Cited

U.S. PATENT DOCUMENTS

| | | | |
|---|---|---|---|
| 2,318,001 | 5/1943 | Linde | 32/14 |
| 4,026,023 | 5/1977 | Fisher | 32/14 |
| 4,273,530 | 6/1981 | Broussard | 433/6 |
| 4,299,568 | 11/1981 | Crowley | 433/6 |
| 4,573,914 | 3/1986 | Nord | 433/18 |
| 4,609,349 | 9/1986 | Cain | 433/6 |
| 4,725,230 | 2/1988 | Harima | 433/6 |
| 4,976,614 | 12/1990 | Tepper | 433/6 |
| 5,022,855 | 6/1991 | Jeckel | 433/6 |
| 5,083,919 | 1/1992 | Quach | 433/6 |
| 5,085,584 | 2/1992 | Boyd | 433/6 |
| 5,096,416 | 3/1992 | Hulsink | 433/6 |
| 5,203,695 | 4/1993 | Bergensen | 433/6 |
| 5,376,001 | 12/1994 | Tepper | 433/6 |

OTHER PUBLICATIONS

Laboratory Services Catalog—1994, Great Lakes Orthodontics, Ltd.
Product Catalog, EOP, Inc., 1993.
Color Selector Guide and Catalog Sheets, TP Orthodontics, Inc., 1989.

*Primary Examiner*—Gene Mancene
*Assistant Examiner*—Jinan Glasgow
*Attorney, Agent, or Firm*—Poms, Smith, Lande & Rose Professional Corporation

[57] ABSTRACT

A removable orthodontic appliance repositions misaligned anterior teeth with a plurality of springs and a labial wire each secured to an acrylic palatal fitting. Each spring has a head portion in the shape of an eyelet which is positioned on the lingual side of an anterior tooth and a foot portion secured to the fitting. The springs provide lingual-to-labial force to the teeth, and the labial wire provides labial-to-lingual force to the teeth. A spring may engage the lingual surface of a tooth to provide active force to urge the tooth labially into a proper position, or may be spaced away from a tooth at a desired position to engage the tooth as it move lingually. The springs may be positioned on a mesial or a distal surface of a tooth to induce rotation. Further, the springs may provide passive resistance to maintain a properly positioned tooth in place. Each spring is made of a single strand of wire which has one end terminating at the head portion and the other end terminating at the foot portion. The orthodontic appliance also has a pair of stress-breaking clasps which dislodge the appliance if the labial wire or the springs are too heavily activated.

20 Claims, 2 Drawing Sheets

REMOVABLE ORTHODONTIC ALIGNER WITH EYELET ARM SPRINGS

BACKGROUND OF THE INVENTION

1. Field of the Invention

The present invention relates to orthodontic appliances for the correction of misaligned teeth. More particularly, the present invention relates to removable orthodontic aligners with a plurality of springs for correcting individual misaligned teeth.

2. Description of the Prior Art

Removable orthodontic appliances have been used since the beginning of modern orthodontic therapy. Dr. Edward H. Angle, considered the Father of Orthodontics, discussed removable orthodontic appliances in the seventh edition of his classic textbook entitled MALOCCLUSION OF THE TEETH, published in 1907. However, the impetus for the evolution of removable orthodontic appliances essentially results from the work of two other men: Dr. C. A. Hawley and Dr. George Crozat.

In order to discuss and describe the invention with accuracy and clarity using dentofacial terminology, a number of definitions will now be provided. In referencing the teeth, the anterior or front teeth of either jaw include the central incisors, which are the two teeth typically foremost in the mouth; the lateral incisors, which are adjacent the central incisors; and the cuspids or canines, which are adjacent the lateral incisors. The posterior or back teeth of either jaw include the bicuspids or premolars, which are posteriorly adjacent the cuspids and naturally in pairs, and the molars. For referencing the various areas of the dentition relative to the mouth, labial refers to that portion of the tooth directed toward or relating to the lips, lingual refers to the tongue, buccal refers to the cheeks, gingival refers to the gums, and palatal refers to the palate. For referencing specific areas of teeth, the occlusal surface is the top surface of the crown of a tooth of one jaw opposing and normally contacting the corresponding tooth of the other jaw; additionally, the mesial portion or surface is the portion of a tooth nearer to the middle or bilateral center of the jaw or mouth, while the distal portion or surface is the portion of a tooth farther from the middle of the jaw. Accordingly, it can be said that each tooth has a labial or buccal surface, a lingual surface, an occlusal surface, a mesial surface, and a distal surface.

Returning to the development of modern orthodontics, in 1919 Dr. Hawley reported the development of a simple and efficient removable retaining appliance that he had developed during the preceding dozen or so years of his clinical practice. This removable retaining appliance, now known as the Hawley retainer, remains essentially unchanged since that time and is still commonly used today. The Hawley retainer was primarily designed as a retaining device and was not intended for anything other than minor tooth movement. However, key components of the Hawley retainer, the labial wire and the acrylic body, provide the foundation on which many modern day appliances are based.

A year after Dr. Hawley's disclosure, Dr. Crozat reported the use of removable appliances as a means of straightening misaligned teeth. His appliance consisted of wires both on the lingual side and on the labial or the buccal side of the teeth. Dr. Crozat attempted to push forwardly or to rotate a tooth through the use of lingual wires. Although Dr. Crozat's appliance caused expansion of the buccal segments, it could be used to improve the alignment of the anterior teeth if space were sufficient.

As orthodontics progressed in sophistication, the concept of growth guidance for children became a part of orthodontic services. In addition to conventional braces, many removable appliances with various spring and wire designs became available. The goal of these appliances was to influence jaw growth rather than to align the teeth individually. These removable appliances are commonly referred to as "functional appliances" and include Activators, Bionators, Frankels, and Sagittals. As these devices are primarily designed to influence jaw growth, they are neither effective in adult orthodontic treatment nor capable of efficiently and predictably aligning crooked teeth.

There are various designs of orthodontic devices known as spring-aligner appliances. These appliances are designed to correct and then to retain minor incisor irregularities such as simple crowding and rotation. For example, if relapse has occurred following orthodontic treatment, the spring aligner may be use to make minor corrections. To construct this type of appliance, the teeth to be aligned are cut off a plaster dentition model and moved into the desired portion. The appliance is then fabricated over the model of repositioned teeth. Orthodontic movement is accomplished by labial and lingual acrylic plates or fittings that have been formed over stainless-steel wire fitted on the repositioned model. These types of appliances cannot be adjusted following fabrication to change any individual tooth position. If different or additional movement is desired, a new appliance must be made. Further, only minor changes can be accomplished by spring aligners as movement of the teeth to be aligned is effected by pressure from the acrylic fitting, not wires directly contacting the teeth. Accordingly, these appliances are not particularly effective for tooth movement and are otherwise highly labor intensive in their fabrication.

Most retainers that are used to align teeth are designed with an acrylic palate or a lingual plate, a labial wire, and a myriad of different posterior retaining clasps to secure the appliance to the posterior teeth. A long recurved flexible spring imbedded in the acrylic fitting usually provides the force to move the teeth. One drawback of such design is that the recurved spring may unexpectedly deflect, thereby changing the intended force direction. Further, if the recurved spring is placed against an incisor which is positioned too far backward, the spring will be ineffective if it distorts vertically, sliding up the lingual surface toward the incisal surface of the incisor. In addition to these drawbacks, it is difficult to pinpoint the pressure to an exact position on the tooth to be moved.

A specific example of an orthodontic appliance which uses springs to move teeth is U.S. Pat. No. 4,026,023 granted to Fisher in 1977. Fisher teaches a T-shaped spring having a vertical portion and a horizontal portion which abuts a tooth. The vertical portion has a pair of spaced tag portions at its lower end for attaching to the orthodontic appliance and a pair of spaced parallel arm portions. The horizontal portion is formed by a pair of oppositely positioned, rounded loop portions with a bridge portion therebetween. This spring design has a drawback in that the fabrication thereof requires multiple bends to form the horizontal and vertical portions. Further, the amount of wire used to form a single spring is substantial as the vertical portion requires a doubling up of the wire, which doubled-up construction also limits the mobility of the spring. Such complicated fabrication and noneconomical use of material are considered to be undesirable aspects of many recently proposed orthodontic devices.

Following my review of many years of development of orthodontic appliances, it has become increasingly obvious to me that an unfulfilled need exists for a removable orthodontic appliance which aligns the anterior teeth while not altering the posterior teeth, an appliance which is easy to construct and which effectively repositions teeth with novel springs. This need has arisen from the fact that a considerable market for such an appliance is driven by a large segment of the population which has crooked or spaced front teeth and very acceptable back teeth. However, despite the efforts of skilled practitioners in the orthodontic arts, the need for such a removable orthodontic appliance remains unfulfilled up to the present.

SUMMARY OF THE INVENTION

An object of the present invention is to provide a removable orthodontic appliance which employs a plurality of eyelet arm springs to correct misaligned teeth. The removable appliance is particularly useful when the posterior teeth of a patient are relatively well positioned while the anterior teeth are misaligned, maloccluded, or otherwise in need of repositioning. As the posterior teeth are not in need of adjustment, they are able to provide anchorage for the appliance as the anterior teeth are being moved.

According to one aspect of the invention, a removable orthodontic appliance includes a fitting which is lingually positioned and anchors the appliance, a labial wire which is secured to the fitting and provides labial-to-lingual force to anterior teeth, and a plurality of springs which are secured to the fitting and provide lingual-to-labial force to anterior teeth. Each spring is made from a single wire which is bent to form a head portion and a foot portion with a shank portion therebetween. The foot portion and part of the shank portion are secured to the fitting, and the head portion is positionable against the lingual side of a tooth.

Another aspect of the present invention is a pair of retaining clasps fixed to the labial wire which engage with or are positioned on respective bicuspids. The clasps serve to stabilize the orthodontic appliance vertically in the mouth of the patient and further provide stress relief, displacing the orthodontic appliance if the labial wire and/or the springs are too heavily activated. The removable orthodontic appliance may be further provided a pair of occlusal rests, particularly if the appliance is intended to correct misaligned teeth of the lower jaw.

A further aspect of the invention lies in the novel design of the springs. The springs are in the shape of eyelet arms with the head portion substantially curvilinear and the foot portion offset from the shank portion. The springs either apply active pressure to urge the teeth labially or provide passive resistance to control the lingual movement of the teeth or maintain the position of a properly positioned tooth as adjacent teeth are being moved. The springs are easily adjustable so that pinpoint pressure may be applied to the teeth to create orthodontic tooth movement. More specifically, the springs are positioned either "short" to be spaced away from a tooth and to receive the tooth at a proper position as it moves lingually or "long" to apply active force to a tooth to move it labially, and the springs may be positioned to the mesial or the distal side of a tooth to control the lingual or the labial movement of the tooth, e.g., to induce rotation.

As the springs are made from a single strand of wire, fabrication is simplified, particularly as one end of the wire terminates at the head portion and the other end of the wire terminates at the foot portion such that the shank portion is essentially a single strand of wire. The diameter of the wire is preferably about 0.026 inch which is much greater than conventional orthodontic spring devices. As such, the springs according to the present invention provide sufficient force without being overly complicated. The inventive springs are further distortion resistant, particularly during occlusion and mastication. Indeed, contrary to the modern orthodontic trend of increasingly complicated oral appliances, the novel springs of the present invention have a sophisticated simplicity, formed of a single 0.12-inch diameter eyelet at one end and a roughly 45-degree to 90-degree bend in the other end. Furthermore, from a production point of view, a variety of eyelet spring arms may be made from a standard length of wire.

Other aspects, features, and advantages of the present invention will become apparent to those skilled in the orthodontic arts from a study of the following detailed description of exemplary embodiments of the invention with reference to the accompanying drawings, particularly advantages relating to the relatively sophisticated yet simple design not only of the eyelet arm springs but of the removable orthodontic appliance as well.

DESCRIPTION OF THE PREFERRED EMBODIMENTS

Figure 1:
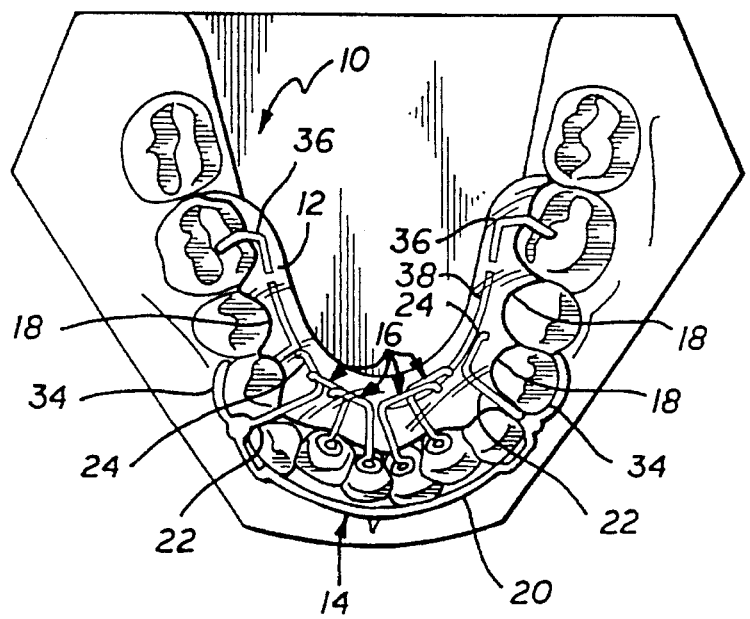
FIG. 1 is a top view of misaligned anterior dentition of the lower jaw with an exemplary embodiment of a removable orthodontic appliance or aligner illustrating the principles of the present invention.
Figure 2:
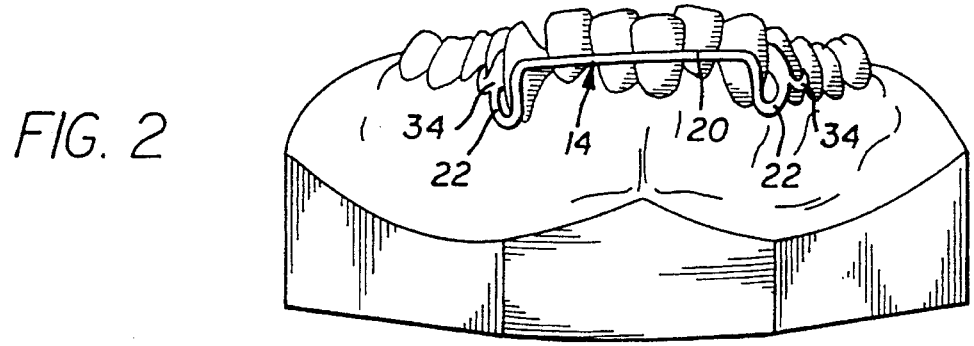
FIG. 2 is a front view of the arrangement of FIG. 1.
Figure 3:
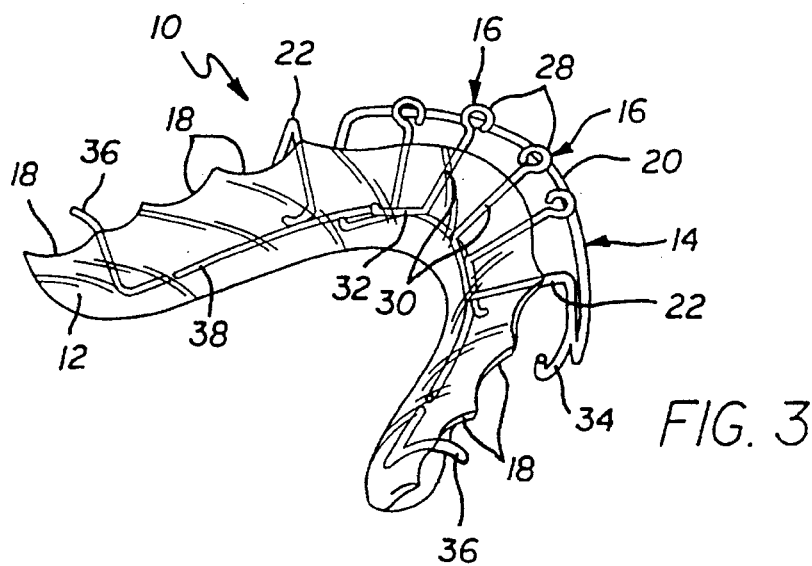
FIG. 3 is a perspective view of a removable orthodontic appliance illustrating the principles of the present invention.

Referring to the drawings, particularly to FIGS. 1, 2, and 3, an exemplary embodiment of a removable orthodontic appliance for aligning anterior teeth is shown and is generally designated by reference numeral 10. The appliance 10 is fit or positioned on dentition of the upper jaw or the lower jaw of a patient, the latter being shown in the drawings. Generally speaking, the removable orthodontic appliance 10 is custom made for the dentition of a particular patient. As shown in FIGS. 1 and 2, the anterior teeth of the plaster model are malaligned or misaligned, maloccluded, and otherwise crooked and undesirable, while the posterior teeth are generally well aligned and properly positioned. This condition of the posterior teeth is preferable for the application or temporary installation of the appliance 10. Further, as for many patients it may be preferable for the appliance 10 to be removable, the appliance 10 is designed without cement or other retaining devices for fastening the appliance in a semipermanent position to the teeth. This not only reduces discomfort to the patient, but this is also more economical and aesthetically appealing. Many people who would otherwise avoid orthodontic work because of unsightly braces, may now undergo orthodontic treatment as the orthodontic appliance 10 may be removed as desired.

The orthodontic appliance 10 generally includes a fitting 12 positioned on the lingual side of the anterior and the posterior teeth for providing anchorage for the appliance 10, a labial wire 14 generally positioned on the labial side of the anterior teeth for providing labial-to-lingual force to the anterior teeth, and a plurality of springs 16 in the shape of eyelet arms positioned on the lingual side of the anterior teeth for providing lingual-to-labial force to the anterior teeth.

The fitting 12 is substantially horseshoe shaped so as to be positionable against the palate or lingual gingiva, and made of a nonreactive material such as plastic, or the like which is plastic or deformable when molten and rigid when hardened. The acrylic fitting 12 has a plurality of recesses or bays 18 each of which conforms to the shape of the inner or lingual surface of a particular posterior tooth such that the bays 18 essentially engage with respective teeth. The plurality of bays 18 in succession conform to the lingual dentition of the posterior teeth, thereby forming a dental-engaging portion of the fitting 12 which occupies the spaces or crevices (i.e., the undercuts) between the posterior teeth. By forming the fitting 12 with the tooth-conforming bays 18, the fitting 12 is retained by the posterior teeth, thereby providing anchorage for the appliance 10 in a front-to-rear (i.e., the labial-to-lingual) direction. The material from which the fitting 12 is made may be of any color or opacity.

The labial wire 14 is preferably made from a single piece of nonreactive steel such as stainless steel or Australian steel which possesses desirable mechanical characteristics and properties commonly known within the orthodontic arts. The labial wire 14 includes a labial portion 20 and a pair of occlusal portions 22. The labial portion 20 is labially positioned and extends across at least the central incisors and the lateral incisors and may further extend or partially extend across the cuspids. The occlusal portions 22 posteriorly extend from respective ends of the labial portion 20 and occlusally extend preferably between the cuspids and the anterior bicuspid, being generally positioned in the crevice therebetween. The ends of the occlusal portions 22 are secured or imbedded into the fitting 12. In order to fix or to imbed the occlusal portions 22 securely in the fitting 12, each of the occlusal portions 22 may have a bend formed at the end thereof, thereby forming an anchoring foot 24. The bend is generally less than 180 degrees and is preferably in the range of approximately 45 degrees to 90 degrees such that each of the feet 24 extends generally posteriorly within the fitting 12. The labial wire 14 may further include a U-shaped portion formed between the labial portion 20 and each of the occlusal portions 22. The U-shaped portions correspond or are positioned relative to a respective cuspid and provide resiliency to the labial portion 20 and stability for the orthodontic appliance 10.

Figure 6:
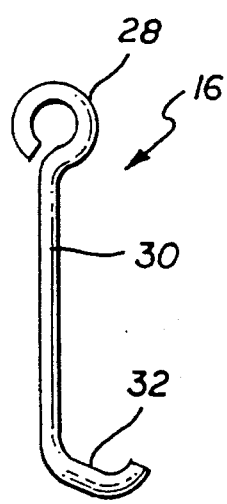
FIG. 6 is a side view of an eyelet arm spring shown in an exemplary embodiment and illustrating the principles of the present invention.

With additional reference to FIG. 6, each of the eyelet arm springs 16 is made from a single strand of wire and includes a head portion 28, a shank portion 30, and an anchoring foot portion 32. The head portion 28 is preferably substantially curvilinear or circular, thereby forming an eyelet. To form the head portion 28, the wire has a bend formed in one end thereof, the bend being greater than about 180 degrees and preferably between approximately 270 degrees to 360 degrees. The shank portion 30 is substantially straight and is in the form of a unitary member, being formed simply of the single strand of wire. To form the foot portion 32, the wire has a bend formed in the other end thereof, thereby offsetting the foot portion 32 from the shank portion 30 by an angle; the bend is less than about 180 degrees and preferably between approximately 45 degrees and 90 degrees. The wire comprising the anchoring foot portion 32 may have another bend near the end thereof such that the foot portion 32 has a small offset projection and takes on a somewhat U-shape or hooked configuration which provides greater anchoring characteristics.

With further reference to FIGS. 1 to 3, the foot portions 32 of the springs 16 are secured, fixed, or imbedded into the fitting 12. Further, a substantial portion of the lower shank portion 30 may also be imbedded in the fitting 12, depending upon the individual orthodontic appliance 10 being made or the individual tooth the spring 16 corresponds to. The portion of each of the springs 16 not imbedded in the fitting 12 projects upwardly and forwardly from the fitting 12 and is positioned adjacent to or engages with the lingual side of an anterior tooth. Depending upon the individual patient dentition, them are preferably four of the springs 16 provided in the appliance 10, one spring for each central incisor and lateral incisor. However, additional springs may be provided for moving or controlling the movement of the cuspids and the individual posterior teeth, although this depends upon the anchorage requirements of the fitting 12 and the cooperation of the patient.

The exemplary embodiment of the removable orthodontic appliance 10 shown in the drawings preferably further comprises a pair of clasps 34 fixedly attached by solder or other suitable means to the labial wire 14 at or near a respective posterior end of the labial portion 20 thereof. The clasps 34 serve to vertically stabilize and retain the appliance 10, and the clasps 34 further provide stress relief, serving as "stress breakers," which will be discussed in more detail below. Each of the clasps 34 is substantially C or U shaped and is made of metal wire similar to that of the labial wire 14. The clasps 34 respectively correspond to the first teeth posterior to the cuspids (typically a first bicuspid unless the patient has had such teeth extracted) and extend generally along the gingival crevice of the respective tooth. The clasps 34 extend to the posterior side of the respective bicuspid and are received in the crevice or fissure between the bicuspid and the next posteriorly disposed tooth, either the second bicuspid or the first molar, depending upon the custom design of the removable appliance 10. Further, as the clasps 34 are respectively disposed on the tooth posterior to the cuspid, the appliance 10 is more stabile than if the clasps 34 were disposed on molars. This increased stability of the appliance 10 results from the positioning of the clasps 34 proximate to the area of active pressure (i.e., the area near the labial wire 14 and the springs 16) or just posterior to the area of active pressure. Such an arrangement eliminates the rocking or pivoting motion common to conventional appliances which attempt to retain the appliance on the molars.

Specifically referencing FIGS. 1 and 3, an exemplary embodiment of the orthodontic appliance 10 may further comprise a pair of molar retainers or occlusal rests 36. The occlusal rests 36 are preferably present if the appliance 10 is providing orthodontic realignment of the lower jaw and are not necessarily needed for an upper-jaw orthodontic appliance in accordance with the present invention. The occlusal rests 36 provide vertical stabilization for the appliance 10. Each of the occlusal rests 36 generally has an anchoring portion which is secured or imbedded into the anchorage-providing fitting 12 and has a hook portion which is occlusally positioned on one of the molars. It is preferable for the molar-retaining occlusal rests 36 to be positioned on the posterior tooth which corresponds to the most posterior bay 18 of the fitting 12. Although the occlusal rests 36 are shown in the drawings to be of a somewhat modified L-shaped configuration, the stabilizing rests 36 may be shaped to suit the particular application of the orthodontic appliance 10 but preferably have an anchoring foot portion as described above relative to the springs 16 to imbed the rests 36 securely in the fitting 12.

The exemplary embodiment of the present invention thus far described may further comprise a brace 38 imbedded within the fitting 12. The brace 38 substantially conforms to the shape of the fitting 12, i.e., is horseshoe shaped, and provides additional rigidity and strength to the fitting 12.

With continued reference to FIGS. 1 and 2, the removable orthodontic appliance 10 is shown applied to a dentition mold of the lower jaw of a patient. As these figures illustrate, the posterior teeth are generally well aligned and in acceptable positions, while the anterior teeth are misaligned and maloccluded, particularly the central incisors and the lateral incisors. As such, the posterior teeth may be used for resistance as the anterior teeth are pushed or pulled into alignment. As clearly illustrated, the fitting 12 conforms to the lingual surfaces of the teeth, to the gingival margin, and to the gums themselves. The plurality of recesses or bays 18 of the teeth-engaging portion of the fitting 12 match or conform to the lingual surfaces of the posterior teeth, preferably at least the bicuspids and the first molar. However, depending upon the individual patient there may be as many bays 18 as needed to provide adequate anchorage. There is preferably a small gap between the fitting 12 and the lingual surfaces of the anterior teeth, particularly the central incisors and the lateral incisors, so that these teeth are permitted to move in a lingual direction without obstruction from the fitting 12. Therefore, as previously mentioned, the acrylic fitting 12 engages with the posterior teeth, "snapping" into place, to provide anchorage for the appliance 10, particularly in the labial-to-lingual direction.

As mentioned above, the labial wire 14 applies labial-to-lingual pressure to the labial surfaces of anterior teeth which are projecting too far forward or are rotated out of proper position, or which otherwise require repositioning. In the example shown in the drawings, the labial portion 20 of the labial wire 14 is bent or formed to contact the left central incisor which is projecting undesirably forward in order to urge this tooth backwardly. The labial portion 20 is formed to contact additionally the cuspids as at least one of these two teeth is also in need of labial-to-lingual movement. As can be seen, the labial portion 20 does not contact the right central incisor or the lateral incisors as these teeth do not need to be moved lingually.

Complementary to the labial arrangement, the springs 16 apply lingual-to-labial pressure to the lingual surfaces of anterior teeth which are projecting too far backwardly or are rotated out of position, or which otherwise require repositioning. It is beneficial to provide a spring 16 even to those teeth which do not require repositioning: as teeth which are being moved lingually move against adjacent teeth which are properly aligned, these properly aligned teeth may be inadvertently displaced and misaligned if there is no spring present to applying a resistive or passive force thereto; teeth may also shift slightly laterally or to the sides during orthodontic correction. Additionally, the springs 16 may be used to control the lingual movement of particular teeth so that these teeth may rotate or be guided into a proper position. This is generally accomplished by either positioning the head portion 28 of the eyelet spring 16 at a central position of the lingual surface of a tooth or at a position slightly offset therefrom to induce and to control rotation, which will be discussed in more detail below.

With regard to the example shown, each of the central incisors and the lateral incisors has a spring 16 either applying lingual-to-labial pressure to or providing passive resistance to the lingual surface thereof. As the left central incisor needs to be moved lingually but does not require rotation, the spring 16 corresponding thereto is spaced away from the tooth at (or is "shortened" to) a position which corresponds to the intended or desired proper position for the left central incisor; accordingly, as the left central incisor moves lingually, it will come in contact with or engage the spring 16 at which time the spring 16 will provide passive resistance in order to restrain the tooth from further lingual movement, maintaining the tooth in the proper position. If the left central incisor also needed to be rotated, the spring 16 corresponding thereto would be spaced away from the tooth and moved slightly mesially or distally to the side so that when the left central incisor contacted the spring 16, the spring 16 would provide passive resistance to either the mesial or the distal surface of the tooth, thereby rotating the tooth as the labial wire continued to urge the tooth lingually.

Additionally, in the sample dentition shown, it is desirable for the two lateral incisors to move labially; accordingly, each of these teeth has a spring 16 applying active lingual-to-labial pressure while the labial wire 14 is space away therefrom. As the right lateral incisor does not need to be rotated, the spring 16 corresponding thereto applies the force generally in the central portion of the tooth. However, as the left lateral incisor needs to be rotated slightly counter-clockwise for proper alignment, the head portion of the spring 16 corresponding thereto is positioned on the mesial surface to the tooth so that rotation will be induced.

Further, the right central incisor also has a spring 16 contacting or abutting the lingual surface thereof, but as this tooth is to remain in its present position, the spring 16 corresponding thereto applies passive resistance to maintain the current desired position. The labial wire 14 may also apply passive resistance to the right central incisor so that the labial movement of the right lateral incisor will not displace the right central incisor. It is noted in passing that in many cases it is desirable to eliminate tight contact or engagement between adjacent teeth so that their relative positions may be shifted more easily. This may be accomplished by sanding the teeth slightly on the sides thereof, which is known in orthodontic practice.

When constructing the removable orthodontic appliance 10 for a particular patient, the practitioner takes an impression and then makes a mold of the patient's dentition. Using the mold, the fitting 12 is formed out of, for example, molten acrylic with the brace 38 imbedded therein. The recesses or bays 18 are particularly formed for the posterior teeth so that the fitting 12 provides adequate anchorage to the appliance 10. The labial wire 14 is then secured to the fitting 12 by imbedding the foot portions 24 of the occlusal portions 22 in the molten acrylic of the fitting 12. Similarly, the eyelet arm springs 16 are secured to the fitting 12 by imbedding the foot portions 16 thereof in the molten acrylic, with the foot portions 16 preferably projecting posteriorly. If the appliance 10 is to be used on the lower jaw of the patient, then the occlusal rests 36 may be secured to the fitting 12 in a manner similar to that described above. Incidentally, it has been found that the springs 16 are more efficient when the eyelet of the head portion 28 opens on the mesial aspect of the tooth.

The practitioner then "fine tunes" or forms the orthodontic appliance 10 to effect the desired dental alignment for the patient. The labial wire 14 is formed to apply pressure to the desired teeth; the springs 16 are bent and positioned to apply active or passive pressure to the desired teeth; and the clasps 34 are formed to properly fit a respective bicuspid. Specifically, the springs 16 are positioned either "short" to be spaced away from a tooth and to receive the tooth at a proper position as it moves lingually or "long" to apply active force to move a tooth labially, and the springs 16 may be positioned to the mesial or the distal side to control the lingual or the labial movement of a tooth, e.g., to induce rotation. The "shortening" and "lengthening" of the springs 16 may be accomplished either by having a longer portion of the shank portion 30 of the spring 16 disposed in the fitting 12 or by opening or closing (e.g., winding up) the eyelet of the head portion 28 of the spring 16.

Regarding the clasps 34, if the labial wire 14 and/or the springs 16 are activated too heavily, i.e., apply too great of pressure to the anterior teeth, then the stabilizing effect of the clasps 34 will be overpowered, and the appliance 10 will be displaced, rendering it uncomfortable and ineffective for the patient. This is the stress-breaking or stress-relief characteristic mentioned above. Accordingly, the retaining clasps 34 provide the removable appliance 10 with increased stability and effectiveness when moving anterior teeth.

Figure 4:
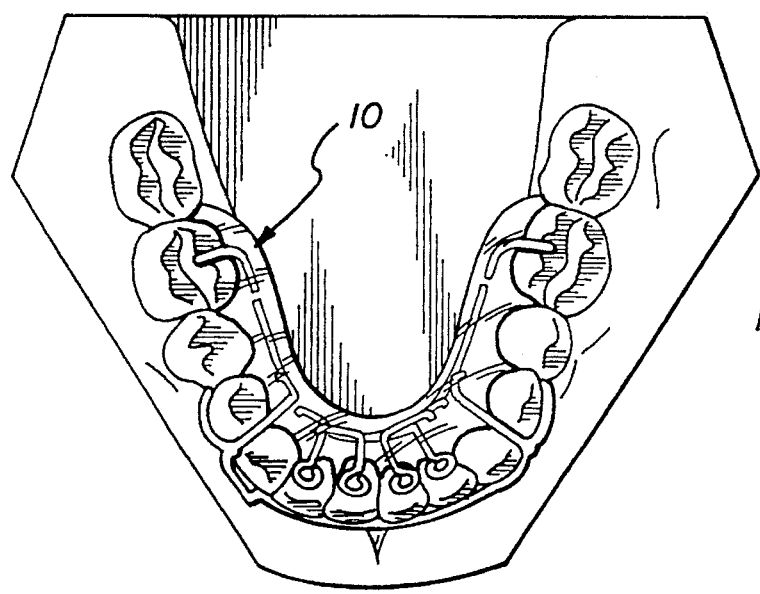
FIG. 4 is a top view of aligned dentition of the lower jaw with an exemplary embodiment of a removable orthodontic appliance of the invention.
Figure 5:
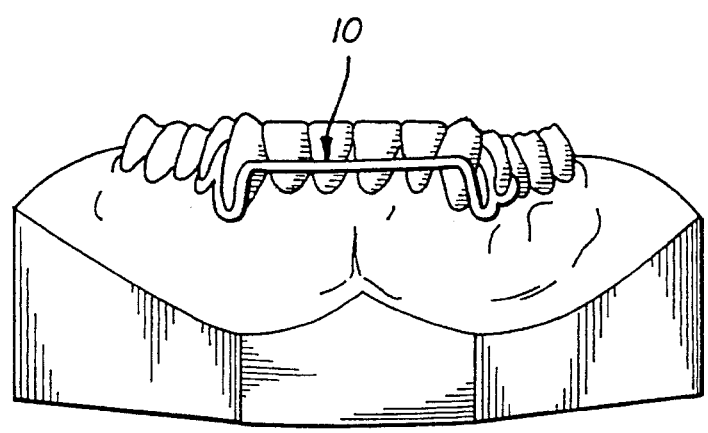
FIG. 5 is a front view of the arrangement of FIG. 4, particularly showing the aligned anterior teeth following the use of the orthodontic appliance of the present invention.

With reference to FIGS. 4 and 5, the removable orthodontic appliance 10 is shown engaged with dentition of the now-aligned anterior teeth of the lower jaw of FIGS. 1 and 2. Whereas FIGS. 1 and 2 illustrate "before" conditions of the teeth, FIGS. 4 and 5 illustrate "after" conditions. As can be seen, the anterior teeth are well aligned and properly positioned. The left central incisor has moved lingually and is positioned next to the right central incisor; the lateral incisors have moved labially and are positioned in alignment with the cuspids and the central incisors. The appliance 10 has been adjusted to act or serve as a passive retainer in that active pressure is no longer applied by the labial wire 14 or the springs 16. This retainer embodiment of the invention simply provides passive resistance in order to maintain the proper alignment achieved by the active pressure-applying orthodontic appliance 10 of FIGS. 1 and 2.

Figure 7:
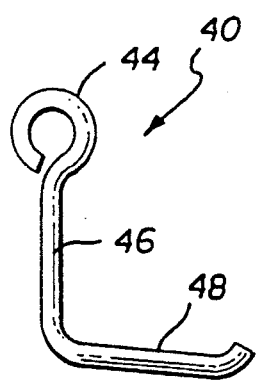
FIG. 7 is a side view of an eyelet arm spring shown in another exemplary embodiment according to the present invention.
Figure 8:
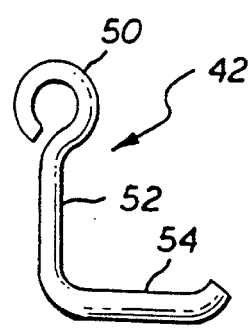
FIG. 8 is a side view of an eyelet arm spring shown in a further exemplary embodiment of the invention.

With further reference to FIG. 6 which illustrates an exemplary embodiment of the eyelet arm spring 16 and with additional reference to FIGS. 7 and 8 which respectively illustrate further exemplary embodiments of eyelet arm springs 40 and 42. Like the embodiment of the spring 16 shown in FIG. 6, the spring 40 is made from a strand of wire and generally includes a head portion 44, a shank portion 46, and an anchoring foot portion 48, and the spring 42 is made from a strand of wire and generally includes a head portion 50, a shank portion 52, and an anchoring foot portion 54; one end of the strand of wire terminates at the head portion, and the other end of the strand of wire terminates at the foot portion. The formation and structure of the springs 40 and 42 are substantially similar to those of the spring 16 described above. However, as can be seen, the respective lengths of the shank portions 30, 46, and 52 and of the foot portions 32, 48, and 54 are different, and the angles between the shank portions and the foot portions are different. These various configurations provide the orthodontic practitioner with a variety of springs 16, 40, and 42 to choose from when constructing and prescribing the proper appliance 10 for a patient.

Specific commercial embodiments of the springs 16, 40, and 42 are made from stainless-steel wire with a diameter in the approximate range of 0.02 inch to 0.03 inch, preferably between 0.024 inch and 0.028 inch; however, the springs are most preferably made from 0.026-inch diameter stainless-steel orthodontic wire. The eyelet of the head portions 28, 44, and 50 has a radius in the approximate range of 0.05 inch to 0.08 inch and is preferably approximately 0.06 inch. The overall length of the strand of wire used to fabricate the springs 16, 40, and 42 may be in the range of seven-eighths inch to one inch and is preferably approximately $15/16$ inch; in any case, the length should be greater than about three quarters of an inch to allow the spring to be properly formed. Given the preferable size of the eyelet of the head portion of the springs, the shank and foot portions of each of the springs 16, 40, and 42 have approximately one-half to five-eighths inch of the wire from which to be formed. As can be seen in FIGS. 6 to 8, the respective lengths of the shank portions 30, 46, and 52 and the foot portions 32, 48, and 54 may be varied according to the practitioners particular need or prescription. In addition, the labial wire 14 may be made from approximately 0.03-inch diameter stainless-steel orthodontic wire, and the brace 38 may be made from approximately 0.06-inch diameter stainless-steel orthodontic wire.

In practice, the fully adjustable eyelet arm springs 16, 40, and 42 may be adjusted to put pressure anywhere on the lingual surfaces of teeth and may be adjusted with various force levels to accomplish light continuous-force orthodontics or heavier intermittent-force orthodontics. Further, the springs 16, 40, and 42 may be adjusted to provide passive pressure to maintain a tooth in its present position while an adjacent tooth is being moved. If a posterior tooth is to be moved, the eyelet of the head portion of the spring is opened by placing force at the gingival margin, perpendicular to the longitudinal axis of the tooth. As a posterior tooth moves buccally, the eyelet is further opened. The point of contact on the tooth may be controlled precisely by varying the shape of the eyelets of the head portions.

In the foregoing disclosure, exemplary embodiments of the present invention are described in detail. However, the removable orthodontic appliance 10 is capable of various modification in structure and operation by one skilled in the art without departing from the inventive principles disclosed herein. For example, the eyelet arm springs 16 may be readily employed in the many nonremovable appliances presently on the market. Further, although is preferable for the springs to be made from stainless steel, the springs may be made from any suitable resilient material such as plastic. In this case, the head portions of the springs may take on various corresponding forms. Accordingly, it is to be understood that the invention is capable of use in various other combinations and arrangements within the scope of the following claims.

What is claimed is:

1. A removable orthodontic appliance for repositioning teeth, comprising:

a horseshoe-shaped plastic fitting having recesses for engaging lingual surfaces of posterior teeth and holding the appliance positioned in a labial-to-lingual direction;

a labial wire secured to said fitting for applying labial-to-lingual force to anterior teeth;

wire clasps secured into said fitting for engaging posterior teeth for holding said appliance in place; and a plurality of metal eyelet springs each formed from a single wire having a single bent wire shank secured into said fitting and having an end of said wire formed into an eyelet with one side of each said eyelet positioned for engaging and applying force to a lingual surface of a different incisor;

whereby said appliance is removable and serves to reposition teeth as a result of the force applied by said eyelets to the incisors.

2. An orthodontic appliance as defined in claim 1 wherein said wires of said springs have a diameter of between 0.024 inch and 0.028 inch.

3. An orthodontic appliance comprising:

a lingually positionable fitting for anchoring said appliance;

a labial wire secured to said fitting for applying labial-to-lingual force; and at least one spring for applying lingual-to-labial force, said spring including a head portion and a unitary shank portion, said head portion being positionable on a lingual surface of a tooth such that lingual-to-labial force is applicable to the tooth, said shank portion being secured to said fitting.

4. An orthodontic appliance as set forth in claim 3 further comprising a pair of stabilizing retaining clasps fixed to said labial wire, each said clasp being positionable on a labial side of a tooth.

5. An orthodontic appliance as set forth in claim 4 wherein said clasps are respectively positionable on teeth posterior to cuspids.

6. An orthodontic appliance as set forth in claim 3 further comprising a pair of stabilizing occlusal rests secured to said fitting.

7. An orthodontic appliance as set forth in claim 3 wherein said head portion is in the form of an eyelet.

8. An orthodontic appliance as set forth in claim 7 wherein said head portion has a radius of approximately 0.06 inch.

9. An orthodontic appliance as set forth in claim 3 wherein said spring further includes a foot portion formed on said shank portion and secured to said fitting, said foot portion being offset from said shank portion.

10. An orthodontic appliance as set forth in claim 9 wherein said foot portion has an offset projection formed thereon.

11. An orthodontic appliance as set forth in claim 3 wherein said spring is made from a wire, said wire having a length of approximately 0.9 inch to approximately 1.0 inch.

12. An orthodontic appliance comprising:

a fitting positionable against a lingual gingiva of a mouth; and a plurality of springs each including a head portion and a shank portion;

said shank portion of each of said springs being secured in said fitting;

each of said springs being positioned in said fitting such that said head portion thereof is positionable on a lingual surface of a respective tooth; and each of said springs being capable of applying force to the lingual surface of the respective tooth.

13. An orthodontic appliance as set forth in claim 12 wherein at least one of said springs is configured for applying active force to a lingual surface of a tooth.

14. An orthodontic appliance as set forth in claim 12 wherein at least one of said springs is configured for applying passive force to a lingual surface of a tooth.

15. An orthodontic appliance as set forth in claim 12 wherein each of said springs is secured in said fitting such that said head portion thereof is positionable on a lingual surface of a respective incisor.

16. An orthodontic appliance as set forth in claim 12 wherein at least one of said springs is secured in said fitting such that said head portion thereof is positionable on a lingual surface of an incisor.

17. An orthodontic appliance as set forth in claim 16 wherein at least one of said springs is secured in said fitting such that said head portion thereof is positionable on a lingual surface of a cuspid.

18. An orthodontic appliance as set forth in claim 16 wherein at least one of said springs is secured in said fitting such that said head portion thereof is positionable on a lingual surface of a posterior tooth.

19. An orthodontic appliance as set forth in claim 12 wherein said head portion is formed as an eyelet, said eyelet being adjustable.

20. An orthodontic appliance as set forth in claim 12 further comprising a labial wire secured to said fitting, said labial wire being capable of applying force to a labial surface of at least one tooth.

* * * * *